US008851669B2

(12) United States Patent
Kapoula et al.

(10) Patent No.: US 8,851,669 B2
(45) Date of Patent: Oct. 7, 2014

(54) DEVICE FOR CAUSING AND/OR REHABILITATING THE BINOCULAR MOTIVITY OF A PATIENT

(75) Inventors: Zoi Kapoula, Paris (FR); Qing Yang, Alfortville (FR); Thomas Eggert, Munich (DE); Gintautas Daunys, Siauliai (LT); Christophe Orssaud, Paris (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 278 days.

(21) Appl. No.: 13/515,792

(22) PCT Filed: Dec. 15, 2010

(86) PCT No.: PCT/EP2010/069830
§ 371 (c)(1),
(2), (4) Date: Aug. 28, 2012

(87) PCT Pub. No.: WO2011/073288
PCT Pub. Date: Jun. 23, 2011

(65) Prior Publication Data
US 2012/0320336 A1    Dec. 20, 2012

(30) Foreign Application Priority Data
Dec. 15, 2009   (FR) ..................................... 09 58994

(51) Int. Cl.
*A61B 3/00*      (2006.01)
*A61B 3/113*     (2006.01)
*A61H 5/00*      (2006.01)

(52) U.S. Cl.
CPC *A61H 5/00* (2013.01); *A61B 3/113* (2013.01); *A61H 2201/5007* (2013.01)

USPC .......................................................... 351/203

(58) Field of Classification Search
CPC ......................................................... A61H 5/00
USPC ........................... 351/200, 203, 205, 220–222
See application file for complete search history.

(56) References Cited

FOREIGN PATENT DOCUMENTS

DE     28 28 532  A1    1/1980

OTHER PUBLICATIONS

Sander., T., "Unterschiedliche Kodierung und Interaktion langsamer konjugierter und diskonjugierter Augenbewegungen im Raum." Internet Citation, Jan. 1, 2006, XP007914029, http://deposit.d-nb.de/cgi-bin/dokserv?idn=984117326&dok_var=d1&dok_ext=pdf &filename=984117326.pdf,pp. 21-29, 74-76.

*Primary Examiner* — Thomas K Pham
*Assistant Examiner* — Brandi Thomas
(74) *Attorney, Agent, or Firm* — Blakely Sokoloff Taylor & Zafman

(57) ABSTRACT

The invention relates to a device for rehabilitating and/or causing binocular motivity through sensory stimulation of a patient, said device including a planar stand (10) that is defined by a longitudinal axis of symmetry (AA'), the stand (10) including a plurality of means for transmitting at least one sensory stimulus, said transmission means including means for viewing a visual stimulus (101-136) and means for transmitting an auditory stimulus adjacent to the means for viewing a visual stimulus. The transmission means are evenly arranged along isovergence arcs (201-204) that are placed along the stand (10). Said device moreover includes a control system (20) that is at least intended for controlling the transmission of said at least one sensory stimulus (101-136).

11 Claims, 9 Drawing Sheets

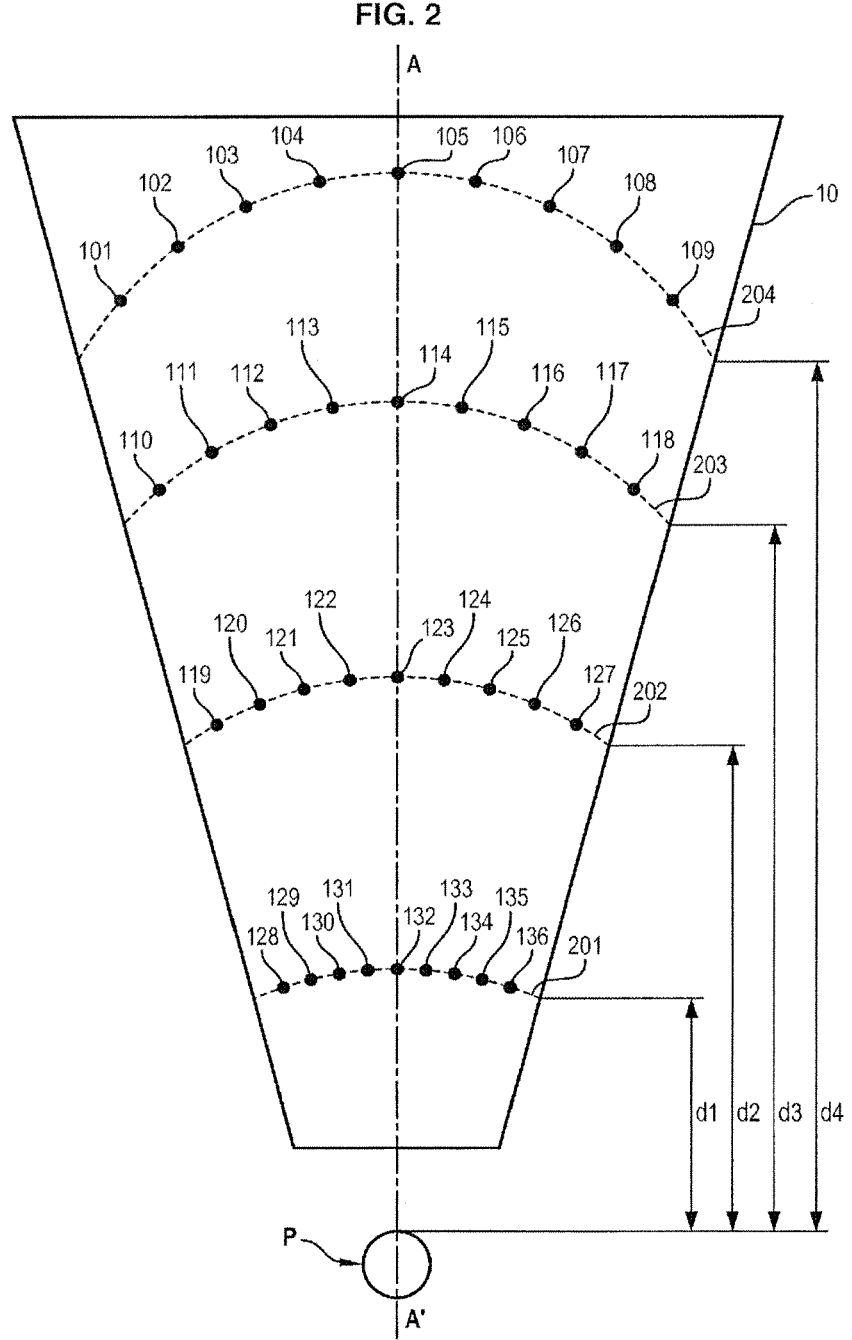

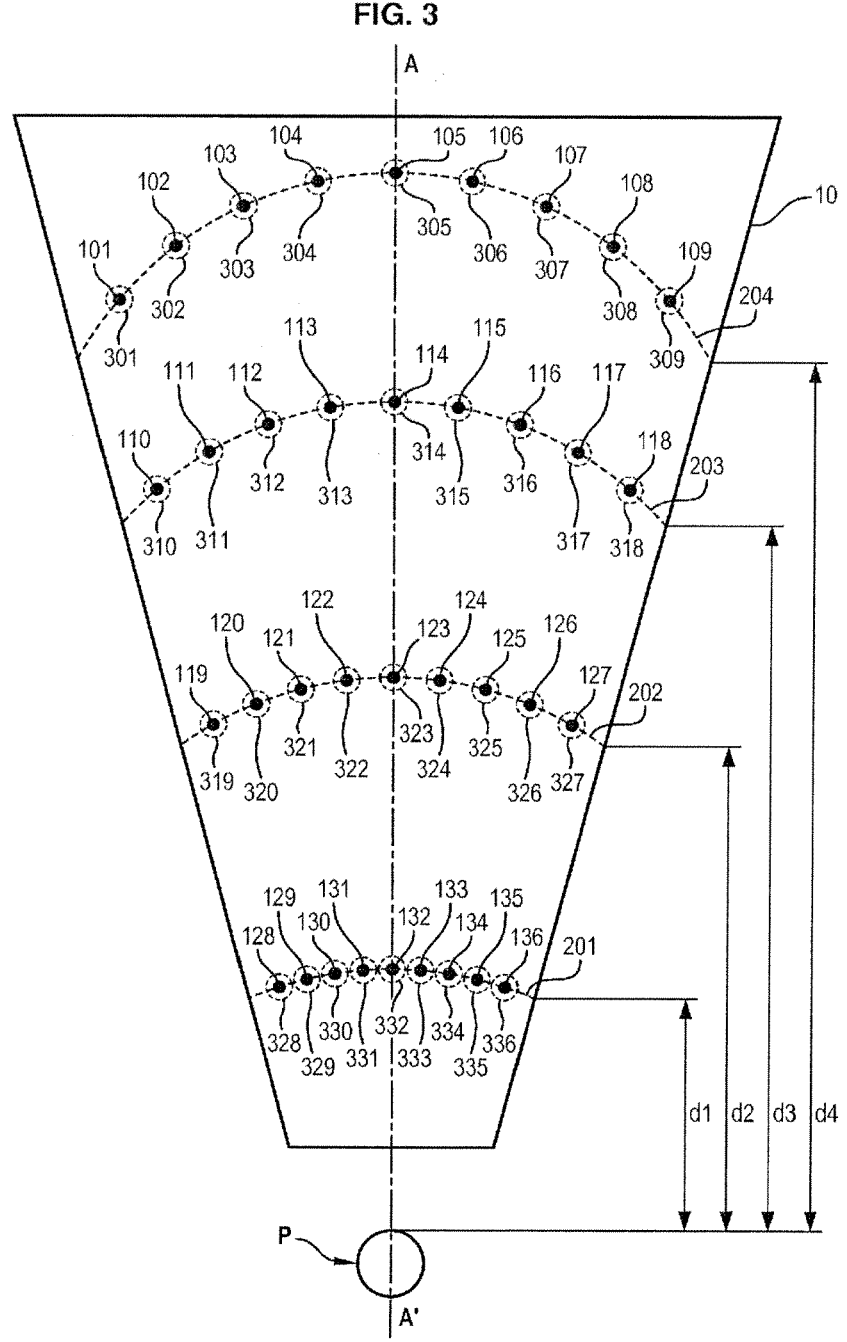

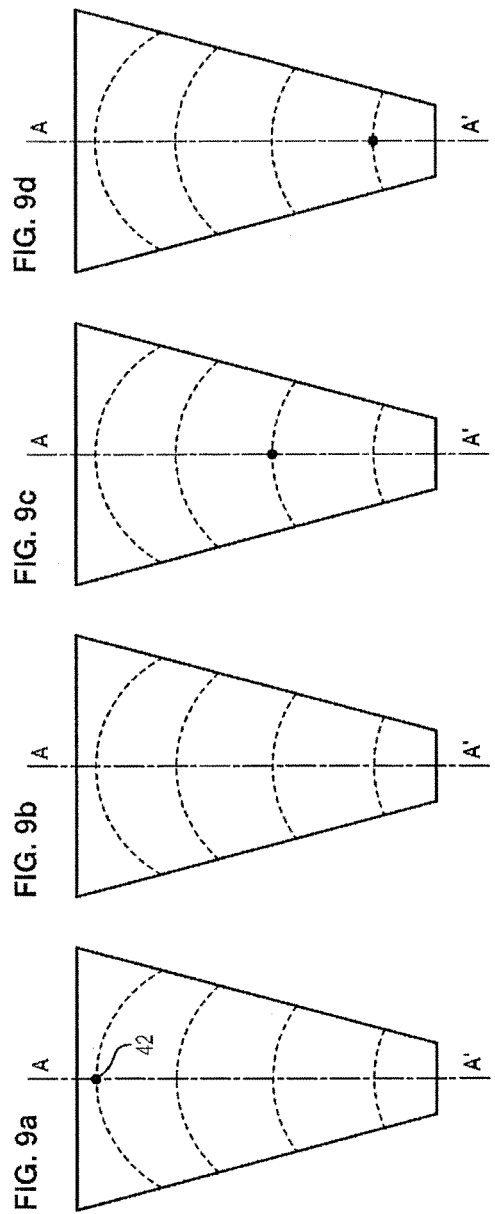
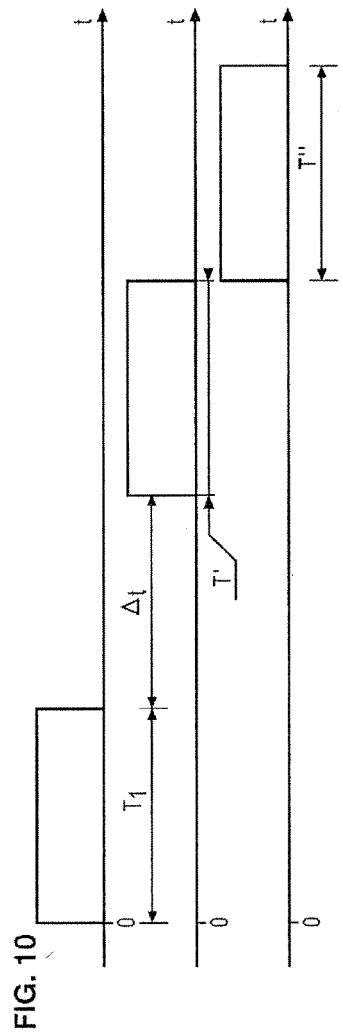

DEVICE FOR CAUSING AND/OR REHABILITATING THE BINOCULAR MOTIVITY OF A PATIENT

This is a non-provisional application claiming the benefit of International Application Number PCT/EP2010/069830 filed Dec. 15, 2010.

GENERAL TECHNICAL FIELD

The invention relates to a binocular motivity rehabilitation and/or training device and also relates to an associated binocular motivity rehabilitation and/or training method, and the invention finds particular application in the treatment of pathologies linked to binocular motivity.

STATE OF THE ART

The training and/or rehabilitation of binocular motivity consist(s) of having a patient perform exercises by means of various devices such as prism bars, synoptophore, etc.

These techniques, however, are limited.

Indeed, they are subjective since they are conditioned by the patient's response to the exercise in question for moving on to the following exercise: is the patient seeing double, for example. This implies that there are no objective measurements because the progress achieved by the patient is measurable only through exchanges between the practitioner and the patient.

In addition, these techniques are static and cannot reeducate/determine the trajectory of eye movements, particularly when certain pathologies are linked to eye movement.

Consequently, the results of orthoptic training/rehabilitation can be aleatory, can depend on the practitioner and on the subject's cooperation.

PRESENTATION OF THE INVENTION

The invention makes it possible to correct the aforementioned drawbacks.

To this end, according to a first aspect, the invention relates to a binocular motivity rehabilitation and/or training device using sensory stimulation of a patient including: a planar stand defined by a longitudinal axis of symmetry, the stand including a plurality of means of transmitting at least one sensory stimulus, said transmission means including means of displaying a visual stimulus and means of transmitting an auditory stimulus adjacent to the means for displaying a visual stimulus, the transmission means being positioned regularly along isovergence arcs located along the planar stand; a control system at least designed to control the transmission of the at least one sensory stimulus.

The device according to the invention enables the rehabilitation and/or training of binocular motivity on the horizontal and vertical axes and in depth and satisfies a strong clinical demand (orthoptics, clinical or independent optometry, optics, visual ergonomics).

The device according to the invention moreover enables the stimulation of physiological synergy, which is the full set of visual cues at the same time: binocular disparity, convergence and accommodation of the lens. The device according to the invention allows vision to be stimulated as it is daily stimulated by combining all physiological resources.

Advantageously, on each isovergence arc, the means of generating a visual stimulus and the means of transmitting an auditory stimulus are arranged in such a way that with each means of displaying a visual stimulus is associated a means of transmitting an auditory stimulus.

The pairing of visual and auditory stimulation means allows simultaneous stimulation of several sensory modalities, particularly important in the case of visual deficiency such as age-related macular degeneration low vision (ARMD low vision).

Other aspects of the device according to the first aspect of the invention are the following:
- the device includes more than two isovergence arcs, preferably four isovergence arcs;
- each isovergence arc includes at least three means of generating a sensory stimulus, preferably nine means of generating at least one sensory stimulus;
- the stand is trapezoidal or triangular;
- the stand can be a fold-out panel, a fan-fold, or made up of several nestable parts;
- the device includes a first isovergence arc at a distance of 20 cm from the patient, a second isovergence arc at a distance of 40 cm from the patient, a third isovergence arc at a distance of 70 cm from the patient, a fourth isovergence arc at a distance of 150 cm from the patient;
- the display means include light-emitting diodes;
- the means for transmitting an auditory stimulus include loudspeakers;
- the means for transmitting an auditory stimulus being designed to transmit, in certain cases, an auditory stimulus having frequencies that differ from one isovergence arc to another;
- the device includes means for coupling with a device for acquiring the patient's eye motions.

According to a second aspect, the invention relates to a method for rehabilitating and/or training binocular motivity by means of a rehabilitation device according to the first aspect of the invention.

The rehabilitation/training method enables rehabilitation/training of binocular motivity on the horizontal and vertical axes, and in depth.

The rehabilitation/training achieved by the method improves the quality of vision of three-dimensional space, but also the deployment of attention and cognitive abilities.

The method of the invention is particularly suited to the following disorders: oculomotor vergence deficit, vertigo, headaches, strabismus, neuro-ophthalmological disorders, neuro-degenerative illness and aging, hyperactivity, dyslexia, as well as to rehabilitation following refractory surgery and rehabilitation in low vision, tinnitus connected with vergence and saccadic motion-vergence interaction problems; could also serve as an alternating neurosensory stimulation tool (left, right) and at different depths for psychotherapists in the field of psychopathology and psychiatry.

Advantageously, by coupling the device of the invention with a device for recording eye motion it is possible to measure objectively the progress achieved by the rehabilitated/trained patient, in particular the physiological change in trajectory of eye motions, their amplitude and accuracy with respect to sensory stimuli.

The device of the invention will include a user brochure for presentation of the various training protocols, as well as a service for discussing various particular pathologies with the principal inventor of the present application.

PRESENTATION OF FIGURES

Further characteristics and advantages of the present invention will appear from the description that follows, which is purely illustrative and not limiting and must be read with reference to the appended drawings wherein:

FIG. 2 illustrates, according to a first embodiment, a bottom view of a stand for the rehabilitation and/or training device for the binocular motivity of a patient according to the invention (display means for visual stimuli);

FIG. 3 illustrates, according to a second embodiment, a bottom view, of a stand for the rehabilitation and/or training device for the binocular motivity of a patient according to the invention (display means for visual stimuli and means of generating auditory stimuli);

Figure 5A:
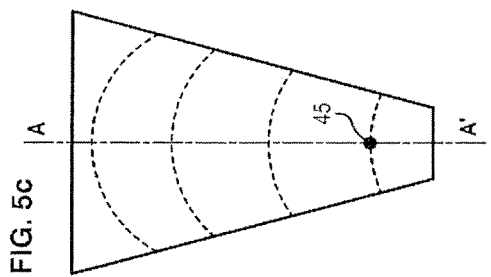
Figure 5B:
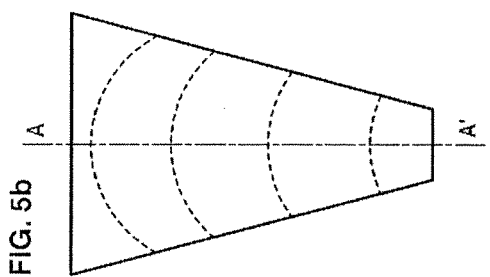
Figure 5C:
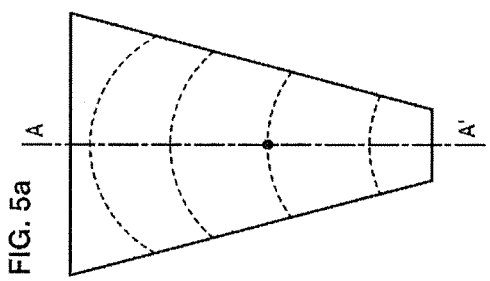
Figure 6:
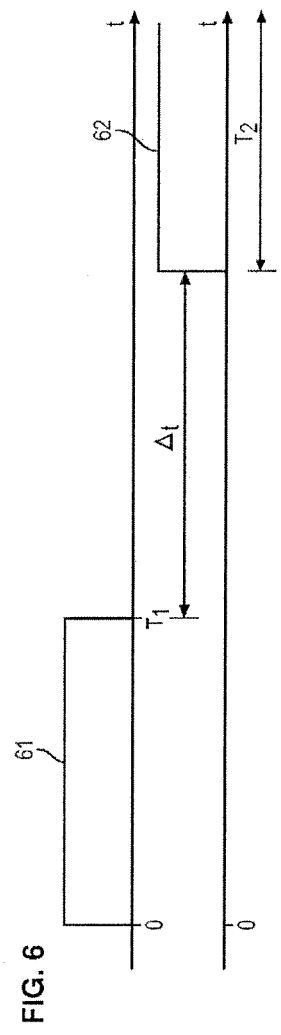
Figure 7A:
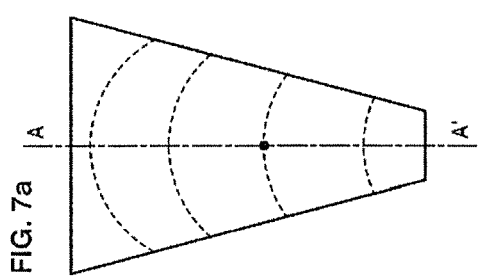
Figure 7B:
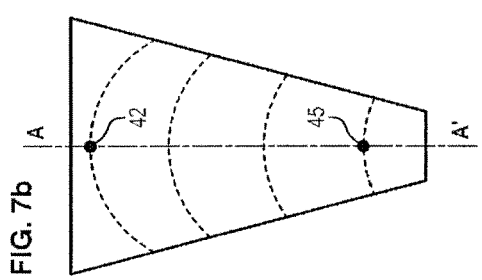
Figure 7C:
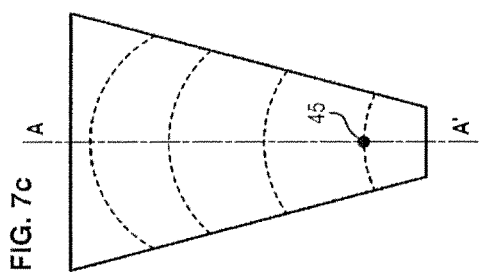
Figure 8:
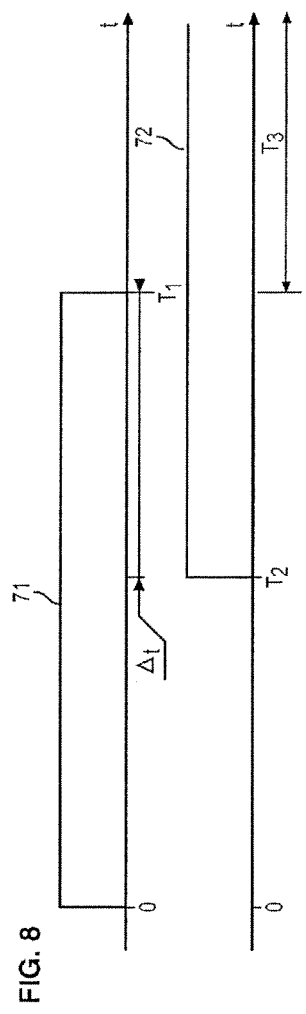
Figure 11A:
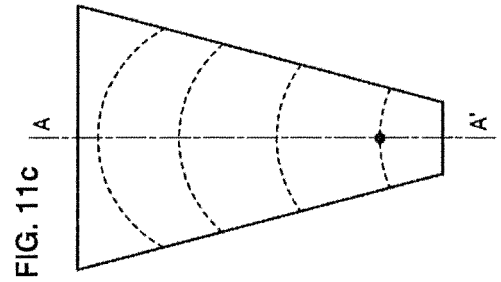
Figure 11B:
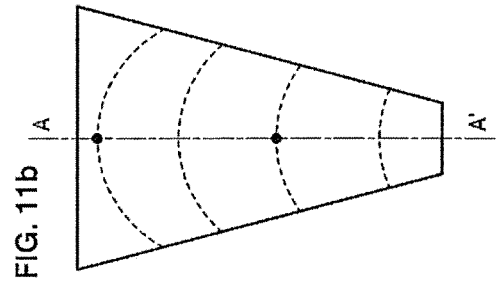
Figure 11C:
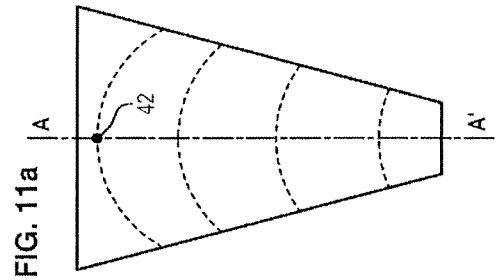
Figure 12:
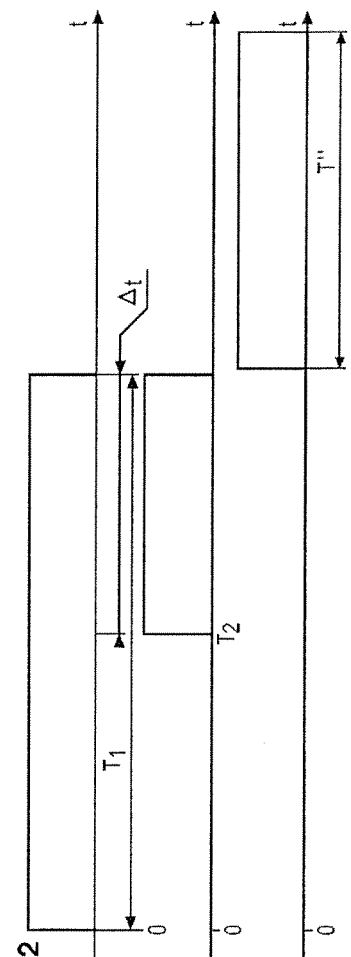
Figure 13A:
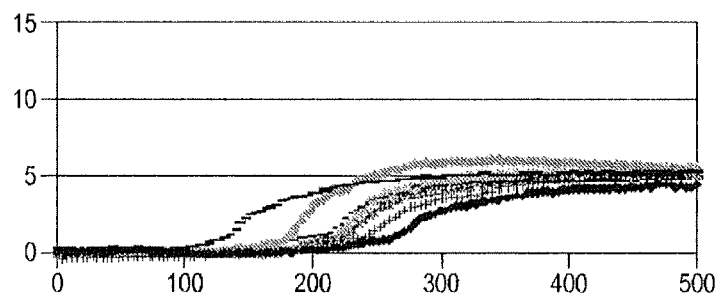
Figure 13B:
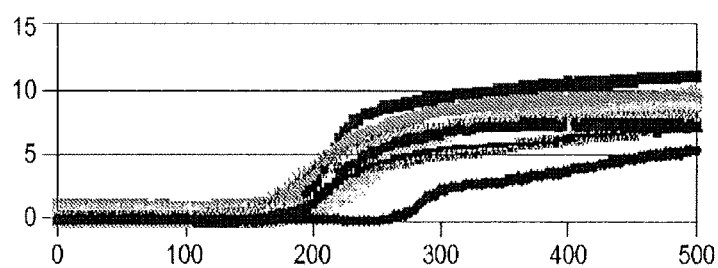
Figure 13C:
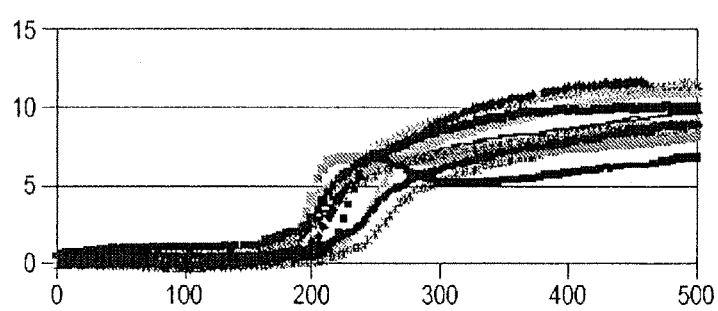

FIGS. 5a, 5b, and 5c illustrate the stand of the invention according to several successive states of a configuration activating a sensory stimulus according to a so-called "gap" sequence;

FIG. 6 illustrates the successive activation periods of a sensory stimulus according to the states of FIGS. 5a, 5b and 5c;

FIGS. 7a, 7b, and 7c illustrate the stand of the invention according to several successive states of a configuration activating a sensory stimulus according to a so-called "overlap" sequence of a single hop type;

FIG. 8 illustrates successive activation periods of a sensory stimulus according to the states of FIGS. 7a, 7b and 7c;

FIGS. 9a, 9b, 9c and 9d illustrate the stand of the invention according to several successive states of a configuration activating a sensory stimulus according to a so-called "gap" sequence of a double-hop type;

FIG. 10 illustrates the successive activation periods of a sensory stimulus according to the states of FIGS. 9a, 9b, 9c and 9d;

FIGS. 11a, 11b, 11c illustrate the stand of the invention according to several successive states of a configuration activating a sensory stimulus according to a so-called "overlap" sequence of a double-hop type;

FIG. 12 illustrates the successive activation periods of a sensory stimulus according to the states of FIGS. 11a, 11b, 11c;

FIGS. 13a, 13b and 13c illustrate the evolution of the response of a patient to training sequences transmitted by means of the device for binocular motivity rehabilitation and/or training of patient according to the invention.

DETAILED DESCRIPTION OF THE INVENTION

Description of the Device

Figure 1:
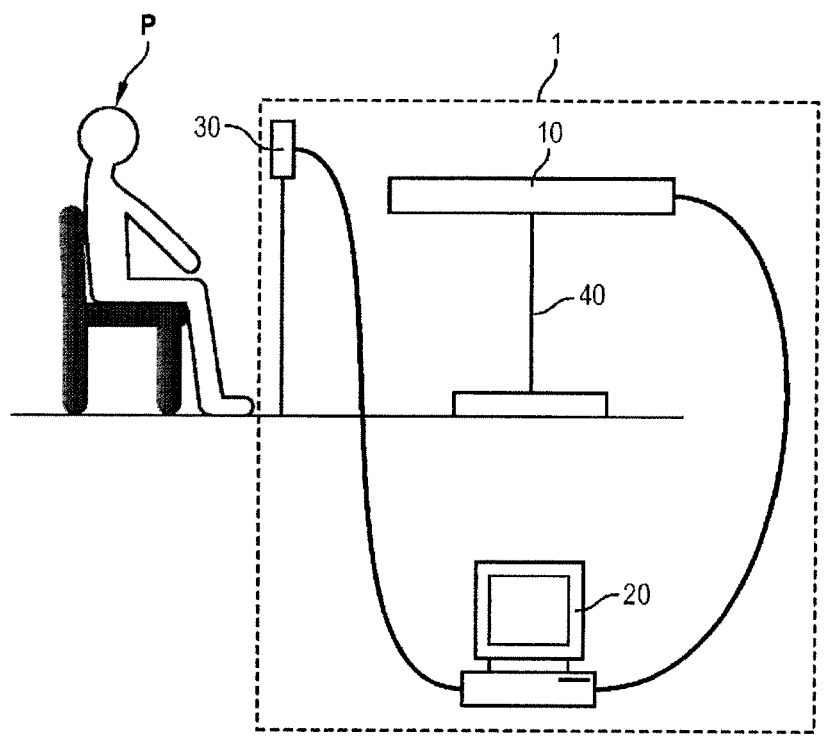
FIG. 1 illustrates a device for rehabilitating and/or training the binocular motivity of a patient according to the invention.

FIG. 1 illustrates a device for binocular motivity rehabilitation and/or training of a patient conforming to the present invention.

The device 1 includes a stand 10 whereon are arranged means of transmitting at least one sensory stimulus, a control system 20 designed to control at least the transmission of at least one sensory stimulus. The control system 20 is for example a PC type computer connected to the stand (particularly to the sensory stimulus transmission means) via an electronic-computer interface (not shown).

It is specified that what is meant by the term sensory stimulus, within the scope of the present invention, is either a visual stimulus or an auditory stimulus or the combination of a visual stimulus and an auditory stimulus.

It is also specified that what is meant by transmission of at least one sensory stimulus is the display of a visual stimulus, the transmission of an auditory stimulus, or the display of a visual stimulus and the transmission of an auditory stimulus together.

The stand 10 can be placed on a table (not shown) or be mounted on a base 40. The base 40 of the stand can be adjustable in height and/or in tilt.

FIG. 2 shows a top view of the stand 10 according to a first embodiment conforming to the present invention. The stand 10 is a planar stand defined by a longitudinal axis of symmetry AA' and includes means 101 through 136 for displaying a visual stimulus arranged regularly along isovergence arcs 201 through 204 arranged along the stand. The stand 10 is shown in FIG. 2, without limitation, in a horizontal position. It is specified that what is meant by isovergence arc are arcs such that the vergence angle of the eyes required to fix them on each sensory stimulus on a given arc is the same. This angle is defined with respect to the position of the patient P at the end of the stand 10.

The stand 10 preferably includes more than two isovergence arcs and very preferably four isovergence arcs 201, 202, 203, 204. In this case, the first isovergence arc 201 is designed to be at a distance d1 of 20 cm from the patient P, the second isovergence arc 202 is designed to be at a distance d2 of 40 cm from the patient P, the third isovergence arc 203 is designed to be at a distance d3 of 70 cm from the patient P, the fourth isovergence arc 204 is designed to be at a distance d4 of 150 cm from the patient P.

The stand 10 can be triangular (not shown) or trapezoidal.

In the case of a trapezoidal stand, the narrow base is of a size comprised between 20 cm and 30 cm, preferably 24 cm, and the wide base is of a size comprised between 110 cm and 130 cm, preferably 120 cm. Moreover, the patient P is intended to be positioned toward the narrow base of the stand.

In the case of a triangular stand, the patient P is intended to be positioned at one vertex of the triangle and two sides extend from the vertex at an included angle comprised between 50° and 60°, typically 54'. The two sides extending from the vertex where the patient P is located are of identical lengths comprised between 160 cm and 190 cm, typically 170 cm.

In order to have a lightweight and foldable stand 10, it can be designed to be in the form of a Chinese fan. Such a stand is divided into several sub-strips separated by fold lines. This stand also includes ribs parallel to the fold lines.

In the case where the stand is in the form of a Chinese fan, the display means for the visual stimuli will be arranged on the ribs of the fan. Thus, as will be understood, in this particular form, the stand 10 has little bulk and is easily transportable.

Advantageously, the stand can be mode of an assembly of several elements, each element corresponding to an isovergence arc. The elements can then be nested. This also contributes to having a stand that occupies little space when it is not in use and that is easily transportable.

The means 101-136 for displaying a visual stimulus are preferably light-emitting diodes (LED). In this case, the LEDs must be harmless to the eye (for example, red LEDs, wavelength 620-625 nm; 20 mA at 2V; 100-200 mcd).

Of course it can be provided that the means for displaying a visual stimulus consist of a light source emitting in the visible band.

As already mentioned, the display means are regularly arranged on the isovergence arcs. Each isovergence arc includes several visual stimulus display means, typically at least three visual stimulus display means, and advantageously nine visual stimulus display means 101 through 109, 110 through 118, 119 through 127, 128 through 136.

The pitch between each display means is comprised between 2° and 8° of visual angle, typically 5°.

The isovergence arcs are symmetrically arranged with respect to the longitudinal axis of symmetry AA' of the stand 10 and are so arranged that the concavity is oriented toward the patient (or toward the vertex of the triangle where the patient is positioned when the stand is triangular or toward the narrow base where the patient is positioned when the stand is trapezoidal).

In addition to the visual stimulus display means, means for transmitting an auditory stimulus can also be provided.

FIG. 3 illustrates a top view of the stand according to a second embodiment conforming to the present invention.

The stand of FIG. 3 includes—in addition to the stand presented above—means 301 through 336 for transmitting an auditory stimulus.

Such auditory stimulus transmission means 301 through 336 are for example loudspeakers and are positioned near a visual stimulus. Consequently, the number of auditory stimuli is equal to the number of visual stimuli (for example nine for each isovergence arc).

The transmission of an auditory stimulus is performed by the control system 20.

Moreover, the rehabilitation/training device can include means 30 for acquiring the eye movements of the patient P, so wit, saccadic eye motions or vergence motions, isolated or in combination. Such acquisition means consist for example of an electro-oculograph or a video-oculograph.

Such means 30 are used to record the movements of the patient's eyes and contribute to optimizing the rehabilitation (as will be discussed below).

An eye movement recording apparatus can be of the known "EOG blue gain, Cambridge Instrument" type. It can also consist of any other video-oculography system of known type (for example Tobii™, Chronos™, Eyelink™, SMI™, See Eye Cam from the University of Munich Hospital).

The device described above can be provided in miniaturized form (with only three isovergence arcs) enabling its use in the home.

Application to Binocular Motivity Rehabilitation/Training of a Patient

The stand 10 presented above in the first and the second embodiment controlled by the control system 20 enables the generation of several visuo-motor training paradigms (visual and possibly auditory stimulation) directed to the patient P located at the end of the stand 10, which is toward the vertex of the triangle where the patient is positioned when the stand is triangular and toward the narrow base where the patient is positioned when the stand is trapezoidal.

The training sequences are generated by an application implemented in the control system 20. Such an application includes several menus for different types of training depending on the pathology or the dysfunction of the patient to be rehabilitated/trained. The sequences enable the training of movements combining direction (in a direction transverse to the longitudinal axis of symmetry AA' of the stand) and depth (in a direction defined by the longitudinal axis of symmetry AA' of the stand), or movements in depth only or even movements in direction only.

Figure 4C:
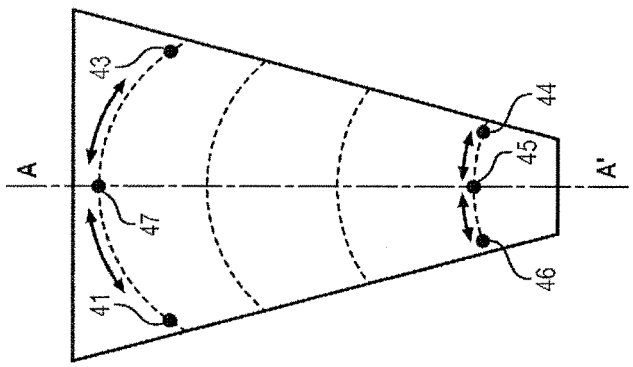
FIGS. 4a, 4b, 4c illustrate bottom views of the stand according to the invention in several operating configurations.
Figure 4B:
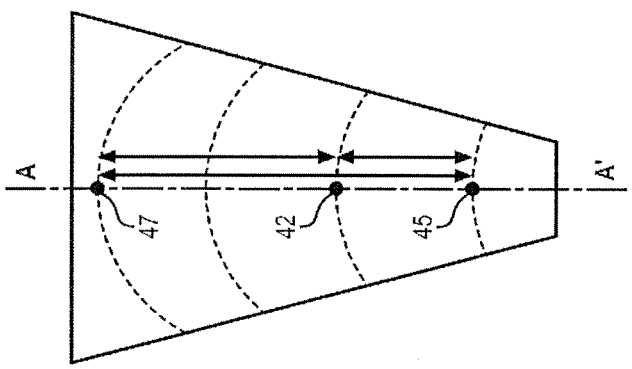
Figure 4A:
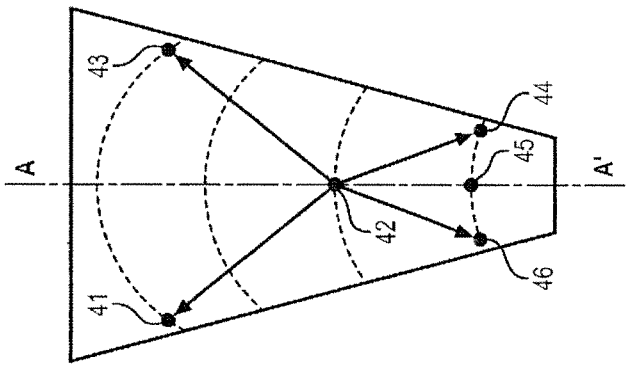

FIGS. 4a, 4h, 4c, illustrate the result of the control of one or more visual stimulus display means and possibly of transmission of the corresponding auditory stimuli.

In these figures, one point corresponds to the activation of a visual stimulus or of an auditory stimulus or of a visual stimulus plus the corresponding auditory stimulus.

FIGS. 4a, 4b and 4c illustrate the state of the stand when a rehabilitation/training sequence using combined saccadic and vergence motions, by pure vergences and by pure saccadic motions, is generated.

The sequence starts with the activation of an "initial" stimulus (visual only or visual plus auditory) in the center of an isovergence arc. Then after a few seconds, typically 2.5 seconds, a "target" stimulus is activated.

Alternatively or complementarily, for each sequence in the case where the activation of a visual target stimulus plus an auditory stimulus is desired, it is possible to provide that the activations are simultaneous or delayed. In the case of delayed activation, an interval comprised between 50 and 150 ms is applied (auditory, then visual).

The "target" stimulus can be transversely offset with respect to the longitudinal axis of symmetry AA' of the stand and be on an isovergence arc other than the "initial" stimulus (which is, for example, activation of the lateral stimulus 41 or 43 after activation of the stimulus 42 or even activation of the lateral stimulus 44 or 46 after activation of the stimulus 42). Such a stimulation triggers in the patient a combined saccadic and vergence motion (see FIG. 4a).

The "target" stimulus can be at the center of another isovergence arc (that is activation of the central stimulus 45 after activation of the central stimulus 42 or activation of stimulus 47 after activation of stimulus 42). Such stimulation triggers in the patient a vergence motion (see FIG. 4b).

The "target" stimulus can be transversely offset with respect to the longitudinal axis of symmetry AA' of the stand on the same isovergence arc as the "initial" stimulus (that is activation of the lateral stimulus 41 or 43 after activation of the central stimulus 47 or otherwise activation of the lateral stimulus 44 or 46 after activation of stimulus 45). Such stimulation triggers in the patient a saccadic motion (see FIG. 4c).

Sequences used for the rehabilitation of a patient are described below.

FIGS. 5a, 5b, 5c and 6 illustrate a so-called "gap" sequence (sequence with an interval) of the single hop type.

FIGS. 7a, 7b, 7c and 8 illustrate a so-called "overlap" sequence (sequence with an overlap) of the single hop type.

FIGS. 9a, 9b, 9c and 10 illustrate a so-called "gap" sequence of the double-hop type.

FIGS. 11a, 11b, 11c and 12 illustrate a so-called "overlap" sequence of the double-hop type.

The so-called "gap" sequence illustrated in FIGS. 5a, 5b, 5c and 6 makes it possible to trigger in the patient a pure vergence motion (along a direction parallel to the longitudinal axis of symmetry AA' of the stand).

FIG. 6 illustrates activation periods of a sensory stimulus (either visual only, or auditory only, or auditory and visual) during the single-hop "gap" sequence.

An "initial" stimulus located at the center of an isovergence arc is activated for a period T1 comprised between 1000 and 2000 ms, preferably 1500 ms, then for a period Δt no stimulus is activated. At the end of the period ☐t, comprised between 100 and 400 ms, preferably 200 ms, a central "target" stimulus of an isovergence arc other than the one activated during the first period T1 is activated during a period T2 comprised between 1000 and 2000 ms, preferably 1500 ms.

The "overlap" sequence illustrated in FIGS. 7a, 7b, 7c and 8 makes it possible to trigger in the patient, alternatively to the "gap" sequence, a pure vergence motion by with the stimulations overlapping.

An "initial" stimulus located at the center of an isovergence arc is activated for a period T1 comprised between 1000 and 2000 ms, preferably 1500 ms, then for a period Δt the "initial" stimulus remains activated while at the same time a "target"

stimulus, located on another isovergence arc, is activated. At the end of the period Δt comprised between 100 and 400 ms, preferably 200 ms, only the "target" stimulus is activated for a duration T3 comprised between 1000 and 2000 ms, preferably 1500 ms.

The "gap" and "overlap" sequences can be of the double-hop type.

The sequence illustrated in FIGS. 9a, 9b, 9c and 9d is a "gap" sequence of the double-hop type. FIG. 10 illustrates the activation periods of a sensory stimulus (either visual or auditory and visual) during the double-hop "gap" sequence.

Following the period Δt of the sequence, the target stimulus is activated only for a short period T' (between 150 and 200 ms); then is followed by the activation of another target stimulus for a period T" of 800 to 1800 ms, preferably 1300 ms. The location of the second stimulus therefore requires an enlargement of the initial motion triggered by the first stimulus.

The sequence illustrated in FIGS. 11a, 11b and 11c is an "overlap" sequence of the double-hop type. FIG. 12 illustrates the activation periods of a sensory stimulus (either visual or auditory and visual) during the double-hop "overlap" sequence.

In this configuration of the "overlap" sequence, the first target stimulus is only activated for a short period T2 (between 150 and 200 ms); following this period Δt another target stimulus is activated for a period T" of 800 to 1800 ms, preferably 1300 ms. As for the "gap" sequence of the double-hop type, the location of the second target stimulus requires an enlargement of the initial motion.

Other training protocols of the double-hop "gap" or "overlap" type will require shortening of the initial motion (not shown).

The training protocol based on sequences of the double hop type is more drastic and very effective because it triggers the implementation by the central nervous system of a new adaptive control (generation of a motor command in response to the final stimulus and not in response to the initial transitory stimulus). The technique can be particularly useful in the case of neuro-ophthalmological pathologies (oculomotor paresis) and in patients with low vision, ARMD.

During rehabilitation, thanks to the means 30 for acquiring eye movement, it is possible to monitor eye movement during rehabilitation and to adjust the sequences as necessary. In particular, it is possible by real-time analysis—during rehabilitation—to determine the optimum visual and/or acoustic stimulation parameters (temporal and spatial) for the training of each patient. For example, in the double-hop protocol described above, the value of the presentation period of the first stimulus is approximate and selected by default based on prior physiological research. It could be adjusted to the patient himself by measuring ahead of time the latency time of his vergence by performing a few sequences of the single-hop type. Thus the training protocol could be personalized.

FIGS. 13a, 13b and 13c illustrate the results obtained on a patient who was rehabilitated according to the method described (single hop with a gap sequence). This is an adolescent presenting with balance disturbances, vertigo and headaches, particularly late in the day. The examination, carried out by the ORL service of the Robert Debré Hospital, showed normal vestibular function, which poses the problem of the origin of the vertigo. The clinical orthoptic examination raised suspicions of an abnormality in the ability of this adolescent to correctly generate vergence motions (convergence and divergence). However, this examination did not allow the abnormalities in the motions to be quantified.

The adolescent was to fix his gaze on a central target 68 cm away, then this target was extinguished and a target appeared randomly closer (25 cm) or farther away (150 cm), which caused convergence and divergence motions respectively. The adolescent performed three successive test blocks (of about 4 minutes each), separated by a pause of about one minute between the blocks.

FIGS. 13a, 13b and 13c show for each of the three blocks the convergence trajectory of the eyes, for the movements going from 68 cm (corresponding to a vergence angle of 5°) to 25 cm (corresponding to a vergence angle of 13.68°). These recordings were carried out with a "Chronos 2D/3D Eye Tracker™" video-oculographic machine.

Delay in the initiation of movements is observed for the first block (see FIG. 13a) (means time 200-250 ms) as well as small motion amplitude (approximately 5°, though the required amplitude is 8.68°). In the second block (see FIG. 13b), initiation is accelerated (mean time 180-200 ms) and the amplitude of the motion increases (approaching the 8.68° required). Finally, maintenance of the conditions noted in the second block is observed in the third block (see FIG. 13c).

Thus, the repetition of these motions with spatiotemporal parameters similar to those of our device shows an objective improvement in the initiation and in the trajectory of the vergence motions. This training protocol (single-hop type gap sequence) was enough for this adolescent presenting with weakness in vergence without vestibular, ocular or neurological pathology.

The invention claimed is:

1. Device for rehabilitating and/or training binocular motivity by sensory stimulation of a patient including:
a planar stand (10) defined by a longitudinal axis of symmetry (AA'), the stand (10) including a plurality of means of transmitting at least one sensory stimulus, said transmission means including means for displaying a visual stimulus (101-136) and means of transmitting an auditory stimulus adjacent to the means for displaying a visual stimulus, the transmission means being arranged regularly along isovergence arcs (201-204) positioned along the stand (10);
a control system (20) designed to at least control the transmission of said at least one sensory stimulus (101-136).

2. The device according to claim 1 including more than two isovergence arcs, preferably four isovergence arcs (201-204).

3. The device according to claim 1 or claim 2, wherein each isovergence arc (201-204) includes at least three means of generating a sensory stimulus, preferably nine means of generating at least one sensory stimulus.

4. The device according to claim 1 or claim 2, wherein the stand (10) is trapezoidal or triangular.

5. The device according to claim 1 or claim 2, wherein the stand (10) is a foldable fan.

6. The device according to claim 1 or claim 2, including a first isovergence arc (201) at a distance (d1) of 20 cm from the patient, a second isovergence arc (202) at a distance (d2) of 40 cm from the patient, a third isovergence arc (203) at a distance (d3) of 70 cm from the patient, a fourth isovergence arc (204) at a distance (d4) of 150 cm from the patient.

7. The device according to claim 1 or claim 2, wherein the display means consist of light sources emitting in the visible band, typically light-emitting diodes.

8. The device according to claim 1 or claim 2, additionally including means (30) of acquiring the eye movements of the patient (P).

9. Method for rehabilitating binocular motivity by means of a binocular motivity rehabilitation device according to claim 1 or claim 2, including a generation of a sequence designed to control the generation of at least one sensory stimulus.

10. The rehabilitation method according to claim 9 wherein the generated sequence controls successively at least two visual stimuli located on different isovergence arcs but having the same angular orientation with respect to the patient so as to generate in the patient a vergence motion.

11. The rehabilitation method according to claim 9, wherein the generated sequence controls successively at least two visual stimuli located on different angular orientations with respect to the patient so as to generate in the patient a saccadic eye motion.

* * * * *